(12) United States Patent
Narayanaswami et al.

(10) Patent No.: US 7,502,068 B2
(45) Date of Patent: Mar. 10, 2009

(54) SENSOR FOR IMAGING INSIDE EQUIPMENT

(75) Inventors: Chandrasekhar Narayanaswami, Wilton, CT (US); Mandayam Thondanur Raghunath, Fishkill, NY (US); Ramon Caceres, New York, NY (US); Stefan Berger, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 757 days.

(21) Appl. No.: 10/874,022

(22) Filed: Jun. 22, 2004

(65) Prior Publication Data

US 2005/0280703 A1 Dec. 22, 2005

(51) Int. Cl.
H04N 5/225 (2006.01)
H04N 7/18 (2006.01)
H04N 9/47 (2006.01)
G03B 17/00 (2006.01)

(52) U.S. Cl. .................. 348/373; 348/82; 348/86; 348/125; 348/143; 396/427

(58) Field of Classification Search ............ 348/82, 348/83, 86, 90, 92, 125, 126, 143, 151, 158, 348/159, 207.1, 211.8, 211.14, 373; 396/427
See application file for complete search history.

(56) References Cited

U.S. PATENT DOCUMENTS

| | | | | |
|---|---|---|---|---|
| RE37,709 | E * | 5/2002 | Dukek | 348/148 |
| 2002/0100053 | A1 * | 7/2002 | Nguyen et al. | 725/105 |
| 2003/0214581 | A1 * | 11/2003 | Ikami | 348/86 |
| 2006/0119704 | A1 * | 6/2006 | Buchhelt | 348/143 |

FOREIGN PATENT DOCUMENTS

JP 2005157706 A * 6/2005

* cited by examiner

Primary Examiner—John M Villecco
(74) Attorney, Agent, or Firm—Michael J. Buchenhorner; Vazken Alexanian

(57) ABSTRACT

A machine comprises an enclosure; a plurality of parts within the enclosure; and a visual conduit for providing a view inside of the enclosure for detection of visible signs of failure of the machine. The concept of a visual conduit encompasses a broad variety of devices including cameras inside the enclosure that provide images of the interior of the enclosure and alternatively selective transparency or translucence of the enclosure relative to at least some of the parts of the machine housed within the enclosure.

2 Claims, 4 Drawing Sheets

SENSOR FOR IMAGING INSIDE EQUIPMENT

CROSS-REFERENCE TO RELATED APPLICATIONS

Not Applicable.

STATEMENT REGARDING FEDERALLY SPONSORED-RESEARCH OR DEVELOPMENT

Not Applicable.

INCORPORATION BY REFERENCE OF MATERIAL SUBMITTED ON A COMPACT DISC

Not Applicable.

FIELD OF THE INVENTION

The invention disclosed broadly relates to the field of machines and more particularly relates to the field of diagnosis of problems in machines.

BACKGROUND OF THE INVENTION

When a machine breaks down, it may be difficult and expensive to repair because disassembly may be required to diagnose the problem. There is also a frequent delay in obtaining parts to replace those broken once the problem has been diagnosed. The resulting down time is also a problem.

Remote monitoring of equipment needs different kind of sensors. Common sensors today include temperature sensors, weight sensors, position sensors, etc. The data from these sensors can be remotely viewed to diagnose the condition of the system. However, there are still situations where these sensors are not adequate to diagnose the problem and is necessary for a human being to open up the equipment and look at it. This process is time consuming and there needs to be a better way. The idea is to use imaging inside the equipment to handle situations that cannot be addressed by the above means.

SUMMARY OF THE INVENTION

Briefly, according to the invention, a machine comprises an enclosure; a plurality of parts within the enclosure; and a visual conduit for providing a view inside of the enclosure for detection of visible signs of failure of the machine. The concept of a visual conduit encompasses a broad variety of devices including cameras inside the enclosure that provide images of the interior of the enclosure and alternatively selective transparency or translucence of the enclosure relative to at least some of the parts of the machine housed within the enclosure.

According to another embodiment of the invention a method for designing a machine comprises the steps of: selecting a first material for an enclosure; and selecting a second material for one or more parts within the enclosure; wherein the selection of the materials permits viewing of the parts under certain conditions.

According to another embodiment of the invention a system comprises an interface for receiving images from remote devices; one or more central servers for storing the images for further analysis using image processing techniques; and a transmitter for further distribution of the images to other destinations.

DETAILED DESCRIPTION

Figure 1:
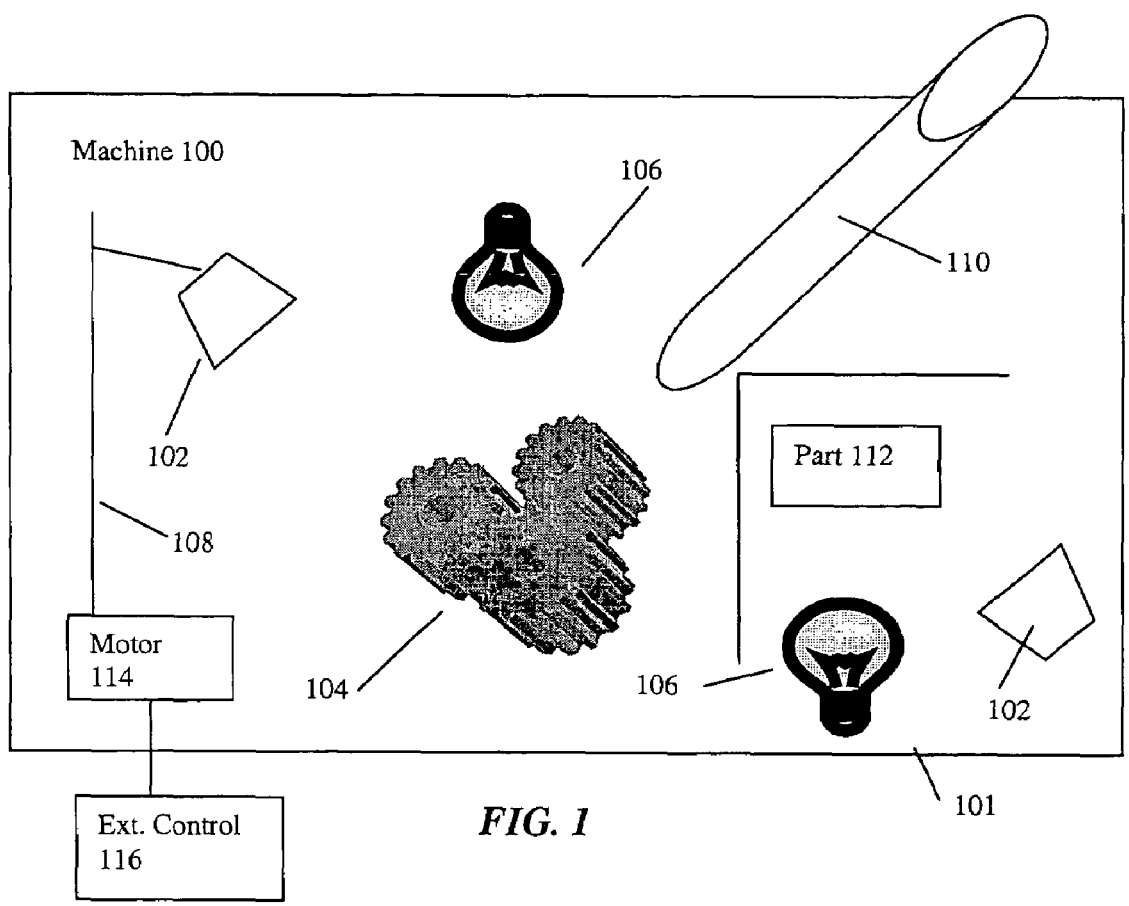
FIG. 1 shows a machine with sensors according to the invention.

FIG. 1 shows a highly-simplified depiction of a machine 100 with sensors according to the invention. The machine 100 comprises an enclosure or housing 101 for machinery 104. In this embodiment, the sensors comprise a set of cameras 102, all located within the machine enclosure 101 to capture images of the machinery 104. Assume that the machine 100 is an expensive piece of equipment such as a printer, magnetic resonance imaging device or the like. In this case a set of parts 104 is malfunctioning. The camera 102 is used to diagnose the problem. In this case assume that the machinery 104 comprises mechanical moving parts and failures can be easily detected by obtaining images of the parts 104 by means of the camera 102 using the light 106 to illuminate the parts. Because the enclosure of the machine need not be opened during a diagnosis operation, the machine can continue to operate showing the cause of failure. Assume that the machine parts 104 are a set of gears and one of the gears is missing a cog. The images produced by the camera 102 are provided to a user outside the machine who can easily determine the cause of the failure. As will be appreciated, the light source 106 may not be required where the camera 102 obtains images using infrared radiation produced by the parts 104 when they are hot as a result of their operation.

The camera 102 can be a still or preferably a video camera with flash, zoom, and other such features. It is preferably controlled by external controls 116. The camera 102 can be mounted on a track 108 and coupled to a motor 114 that is controlled by the external controls 116. The user is presented with the images provided by the camera 102 and can thus interactively control the orientation and movements of the camera to provide the desired images of the machine parts 104.

The camera 102 has a unique identifier (ID) and a wired or wireless link to the outside world for communication with a user. The unique identifier is transmitted to the outside world so that each machine can be identified from other nodes in the network. Alternatively, the camera 102 may be programmed to move automatically providing a set of images that may be stored and later viewed on demand to determine what caused a failure in the past. The light 106 can also be programmed to move automatically or can be moved manually by means of the external control apparatus 116.

An alternative image conduit is provided by a tube 110 having an internally reflective surface (preferably fiber optics) that transmits an image or images of the interior of the machine 100 to the outside. Such a tube 110 can include a camera and light as well. The tube is preferably flexible so that it can negotiate winding paths throughout the machine 100.

The cameras can be placed in locations where even highly obscured parts (such as part 112) can be imaged.

Figure 2:
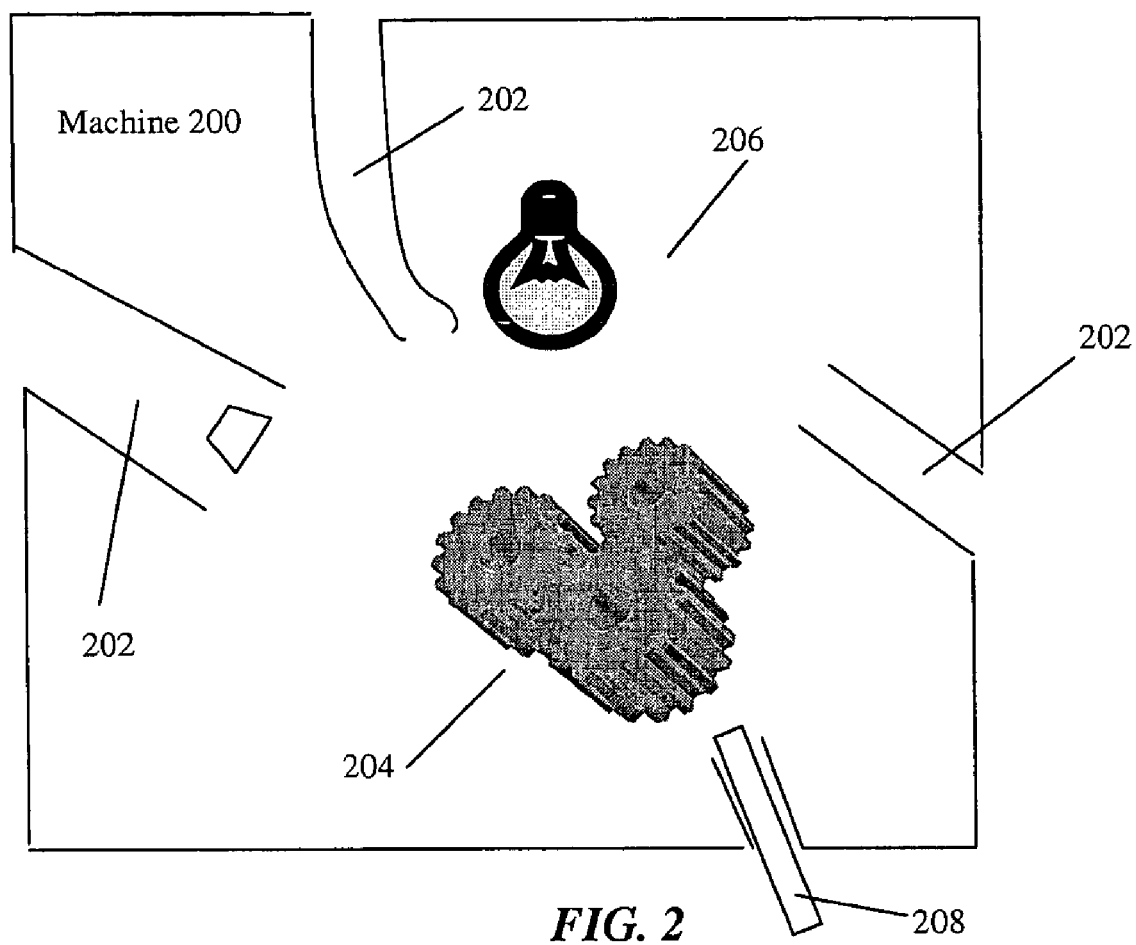
FIG. 2 shows a highly-simplified depiction of a machine according to another embodiment of the invention.

Referring now to FIG. 2, there is shown a machine 200 according to another embodiment of the invention. In this embodiment, the visual conduit comprises a plurality of pathways or canals 202 that are provided throughout the machine to provide images of its interior. As in the case depicted in FIG. 1, a canal 202 provides an image of the machine parts 204 to its users to assist in determining whether the parts are operating properly. A light source 206 provides illumination where necessary. Optional camera guide rails or paths 208 are provided in one of the canals 202 to allow for movement of a camera (not shown) to locations required for providing the desired images. Thus, a camera can be sent through the pathways 208 for providing images throughout the inside of the machine.

Figure 3:
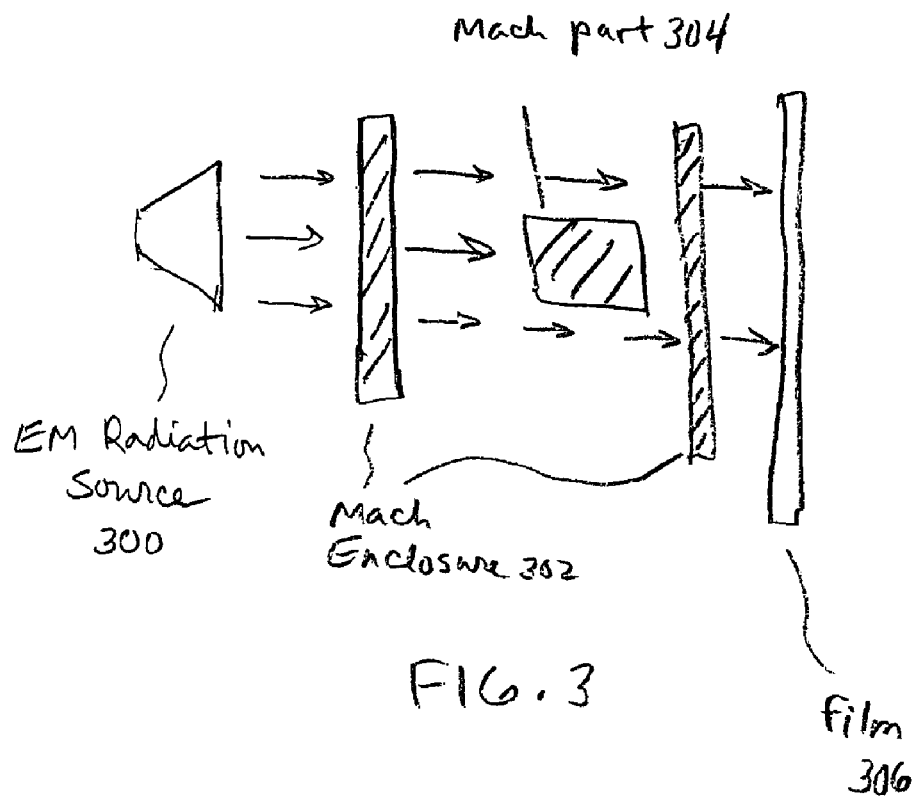
FIG. 3 shows a cross-section of a machine with parts made form materials with different properties.

Referring to FIG. 3, there is shown another embodiment of the invention wherein the visual conduit comprises a machine enclosure 302 made from a material that is transparent to a source of electromagnetic radiation (EMR) 300 at one or more frequencies such as x-ray frequencies. Thus the radiation source 300 provides x-rays that pass through the enclosure 302 relatively unimpeded but are substantially blocked by a machine part 304 that is made from a different material that is opaque to the EMR. The result is an image of the machine part 304 that can be captured at a sensor 306 outside the enclosure 302. An example of a sensor is a film that is sensitive to x-rays. The sensor can be located inside the enclosure 302 and connected to the outside by a communication link to provide the images acquired. The film 306 can be optionally replaced by a sensor (such as charge-coupled devices) that detects the EMR that passes through enclosure 302, and provides the image to the world outside the enclosure.

Figure 4:
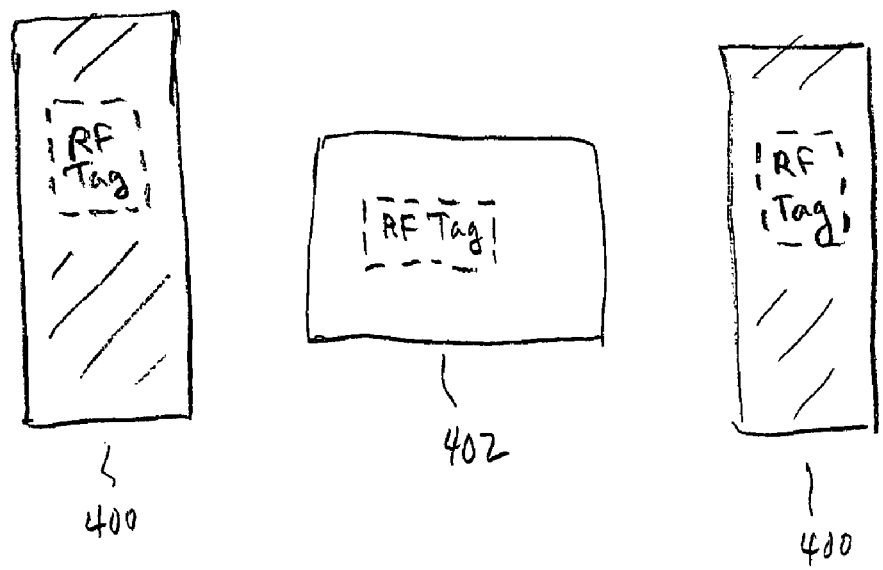
FIG. 4 shows a machine with parts made form materials with different properties wherein RF-tags are embedded in the parts to identify the materials.

Referring to FIG. 4, there is shown another embodiment of the invention wherein the machine enclosure 400 is made from a different material than the interior parts 402 and radio-frequency tags are embedded in the parts to provide an indication of the material from which they are made. An RF-tag reader (not shown) can be used from outside the enclosure 402 to read the information stored in the RF-tag. This provides a user information that can be used to determine the properties of the materials so that the user can select an appropriate visualization tool (e.g. x-rays).

Figure 5:
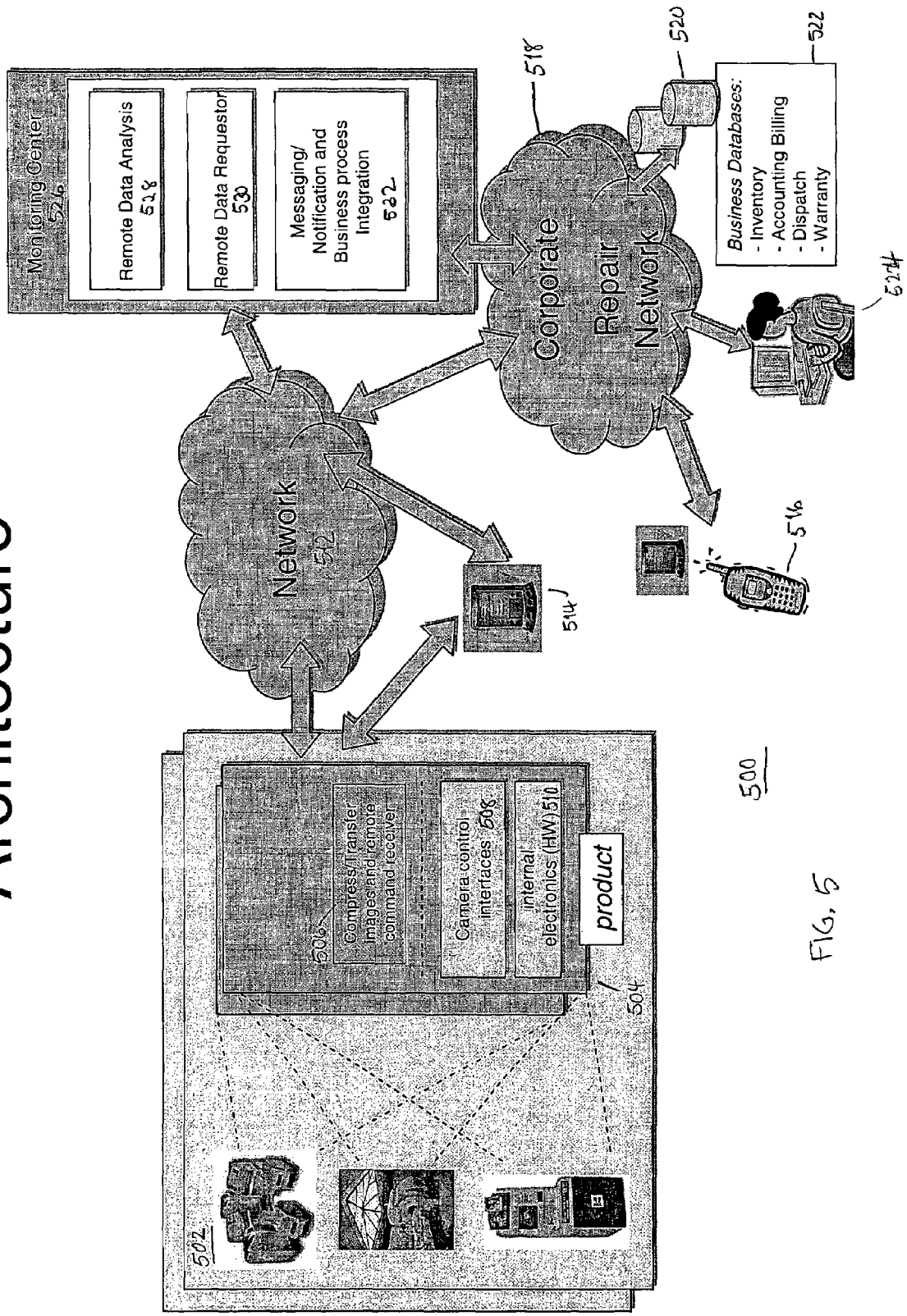
FIG. 5 shows system architecture according to the present invention.

FIG. 5 shows system architecture 500 of a system that uses the invention to diagnose problems in machines. The system 500 monitors a set of equipment 502 for purposes of maintaining its operation. The equipment 502 comprises machines having parts within their interiors that are monitored by means of visual conduits as discussed above. The equipment 502 is typically expensive to repair because of the troubleshooting required. Each item of equipment 502 interfaces with a network 512 by means of an interface 504. The interface 504 comprises a module 506 for compressing/transferring images and receiving remote commands. A module 508 comprises camera control interfaces for controlling the location and orientation of the cameras located inside the equipment and a module 510 comprising the internal electronics for controlling the operation of the visual conduits.

The interface 504 is linked, via a wireless link, with a personal digital assistant 514; and via the network 512 to a monitoring center 526. The monitoring center 526 comprises: a remote data analysis module 528; a remote data requester 530; and a messaging/notification and business process integration module 532. The remote data analysis module 528 receives data originating from the monitored machine 502 and transmits the data to a corporate repair network 518. From there, it can be stored in persistent storage 520, in proprietary business databases 522, downloaded to mobile devices 516 such as cell phones, or downloaded directed to the systems of users 524 who monitor the performance of the machines 502. The remote data requester 530 can be used by a user to request data gathered by sensors monitoring the machines.

The messaging/notification and business process integration module 532 is used to coordinate the tasks performed using various enterprise business applications that may not have compatible syntax or data structures. Module 532 can comprise software such as IBM's WebSphere Business Integration™ software or MQ Series.

What has been shown and discussed is a highly-simplified depiction of a programmable computer apparatus. Those skilled in the art will appreciate that other low-level components and connections are required in any practical application of a computer apparatus. Therefore, while there has been described what is presently considered to be the preferred embodiment, it will be understood by those skilled in the art that other modifications can be made within the spirit of the invention.

We claim:

1. A machine comprising:
   A) an enclosure, and disposed within the enclosure:
      a plurality of parts, wherein at least one of the parts is a mechanical moving part;
      at least one movable light source that illuminates the at least one mechanical moving part;
      at least one imaging system placed inside the enclosure and positioned to capture and transmit images of a visible indicator of failure of the at least one mechanical moving part, wherein the at least one imaging system comprises:
         at least one feature selected from a group consisting of: flash, zoom, still photography, light sensors, heat sensors and video;
         a unique identifier; and
         a wireless link for transmitting the images to an external source;
      a track sustaining the at least one imaging system, the track positioned such that when the at least one imaging system is positioned on the track, a lens of the at least one imaging system has a line of sight to the at least one mechanical moving part;
      a motor coupled with the track that enables movement of the imaging system along the track to locations required for providing desired images; and
   B) an external controller disposed outside of the enclosure, and operatively and wirelessly coupled with the at least one imaging system, the at least one movable light source, and the motor;
      wherein the external controller is operable to interactively control orientation and movement of the at least one imaging system, the at least one movable light source, and movement of the motor to the locations as required for providing the desired images; and
      wherein the external controller controls orientation and movement responsive to previously transmitted images indicating presence or absence of the visible indicator of failure of the at least one mechanical moving part.

2. An imaging system for monitoring machinery, the imaging system comprising:
   A) at least one camera disposed inside an enclosure of the machinery and positioned to capture and transmit images of a visible indicator of failure of at least one mechanical moving part inside the machinery, wherein the at least one camera comprises:

i) at least one feature selected from a group consisting of: flash, zoom, still photography, light sensors, heat sensors and video;

ii) a unique identifier; and iii) a wireless link for transmitting the images to an external source;

a track sustaining the at least one camera, the track positioned such that when the at least one camera is positioned on the track, a lens of the at least one camera has a line of sight to the at least one moving part;

a motor coupled with the track that enables movement of the camera along the track to locations required for providing desired images; and at least one movable light source that illuminates the at least one moving part; and B) an external controller disposed outside of the enclosure, and operatively and wirelessly coupled with the at least one camera, the at least one movable light source, and the motor;

wherein the external controller is operable to interactively control orientation and movement of the at least one imaging system, the at least one movable light source, and movement of the motor to the locations as required for providing the desired images; and wherein the external controller controls orientation and movement responsive to previously transmitted images indicating presence or absence of the visible indicator of failure of the at least one mechanical moving part.

* * * * *